(12) United States Patent
Bodas et al.

(10) Patent No.: US 12,037,313 B2
(45) Date of Patent: Jul. 16, 2024

(54) PROCESS AND SYSTEM FOR PRODUCING ETHYLENE AND AT LEAST ONE OF BUTANOL AND AN ALKYL TERT-BUTYL ETHER

(71) Applicant: SABIC Global Technologies B.V., Bergen op Zoom (NL)

(72) Inventors: Vijay Dinkar Bodas, Riyadh (SA); Guillermo Leal, Riyadh (SA); Mohammed Bismillah Ansari, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 58 days.

(21) Appl. No.: 17/292,261

(22) PCT Filed: Nov. 20, 2019

(86) PCT No.: PCT/IB2019/059984
§ 371 (c)(1),
(2) Date: May 7, 2021

(87) PCT Pub. No.: WO2020/104967
PCT Pub. Date: May 28, 2020

(65) Prior Publication Data
US 2021/0380515 A1    Dec. 9, 2021

Related U.S. Application Data

(60) Provisional application No. 62/769,864, filed on Nov. 20, 2018.

(51) Int. Cl.
| | | |
|---|---|---|
| *C07C 41/06* | (2006.01) | |
| *C07C 4/02* | (2006.01) | |
| *C07C 5/05* | (2006.01) | |
| *C07C 5/32* | (2006.01) | |
| *C07C 5/42* | (2006.01) | |
| *C07C 6/04* | (2006.01) | |
| *C07C 7/04* | (2006.01) | |
| *C07C 29/04* | (2006.01) | |

(52) U.S. Cl.
CPC ........... *C07C 41/06* (2013.01); *C07C 4/02* (2013.01); *C07C 5/05* (2013.01); *C07C 5/32* (2013.01); *C07C 5/42* (2013.01); *C07C 7/04* (2013.01); *C07C 29/04* (2013.01); *C07C 6/04* (2013.01)

(58) Field of Classification Search
None
See application file for complete search history.

(56) References Cited

U.S. PATENT DOCUMENTS

| | | |
|---|---|---|
| 3,061,654 A | 10/1962 | Gensheimer et al. |
| 3,797,690 A | 3/1974 | Taylor et al. |
| 3,849,082 A | 11/1974 | Kozlowski et al. |
| 3,912,463 A | 10/1975 | Kozlowski et al. |
| 4,324,936 A | 4/1982 | Mikulicz |
| 4,334,890 A | 6/1982 | Kochar et al. |
| 4,336,046 A | 6/1982 | Schorre et al. |
| 4,356,339 A | 10/1982 | Imaizumi et al. |
| 4,408,085 A | 10/1983 | Gottlieb et al. |
| 4,423,251 A | 12/1983 | Pujado et al. |
| 4,436,946 A | 3/1984 | Smitny |
| 4,455,445 A | 6/1984 | Neuzil et al. |
| 4,499,313 A | 2/1985 | Okumura et al. |
| 4,540,831 A | 9/1985 | Briggs |
| 4,754,078 A | 6/1988 | Vora et al. |
| 4,773,968 A | 9/1988 | O'Connell et al. |
| 4,783,555 A | 11/1988 | Atkins |
| 4,797,133 A | 1/1989 | Pujado |
| 4,927,977 A | 5/1990 | Child et al. |
| 5,227,553 A | 7/1993 | Polanek et al. |
| 5,254,748 A | 10/1993 | Hensley et al. |
| 5,382,707 A | 1/1995 | Rubin et al. |

(Continued)

FOREIGN PATENT DOCUMENTS

| | | |
|---|---|---|
| CA | 2018524 A1 | 12/1990 |
| CN | 1044804 C | 8/1999 |

(Continued)

OTHER PUBLICATIONS

Fuel Additives Selection Guide: Types, Features, Applications, Engineering 360, 4 pages, obtained May 11, 2022, http://www.globalspec.com/learnmore/materials_chemicals_adhesives/industrial_oils_fluids/fuel_oil_fluid_additives (Year: 2022).

Ansari et al. U.S. Appl. No. 17/054,906, entitled "Method of Producing a Fuel Additive With a Hydration Unit", filed with the USPTO on Nov. 12, 2020.

Bender et al.; "Selective Hydrogenation in Steam Cracking"; 21st Annual Saudi-Japan Symposium; Catalysts in Petroleum Refining & Petrochemicals; King Fahd University of Petroleum & Minerals; 2011; Abstract only; pp. 1-3.

Brockwell et al.; "Synthesize ethers"; Hydrocarbon Processing, vol. 70, No. 9; 1991; pp. 133-141.

(Continued)

*Primary Examiner* — Rosalynd A Keys
(74) *Attorney, Agent, or Firm* — CANTOR COLBURN LLP

(57) ABSTRACT

A process for producing ethylene and at least one of butanol and an alkyl tert-butyl ether from field butane includes separating the field butane into an n-butane stream and an isobutane stream; cracking the n-butane stream to obtain a cracked product stream comprising n-butane, 1-butene, 2-butene, butadienes, or a combination comprising at least one of the foregoing; and at least one of the following: (1) separating the cracked product stream to obtain a butane stream and a butene stream, and reacting the butene stream with water to obtain a fuel additive comprising butanol, and (2) dehydrogenating the isobutane stream in a dehydrogenation unit to form an isobutene stream and reacting the isobutene stream with an aliphatic alcohol to produce an alkyl tert-butyl ether.

18 Claims, 1 Drawing Sheet

(56) References Cited

U.S. PATENT DOCUMENTS

| | | | |
|---|---|---|---|
| 5,523,502 A | 6/1996 | Rubin | |
| 5,563,299 A | 10/1996 | Paludetto et al. | |
| 5,628,880 A | 5/1997 | Hearn et al. | |
| 5,672,795 A | 9/1997 | Vora et al. | |
| 5,864,052 A * | 1/1999 | Nierlich | C07C 41/06 |
| | | | 568/454 |
| 5,877,365 A | 3/1999 | Chodorge et al. | |
| 5,898,091 A | 4/1999 | Chodorge et al. | |
| 5,955,640 A | 9/1999 | Paludetto et al. | |
| 7,227,047 B2 | 6/2007 | Risch et al. | |
| 7,473,812 B2 | 1/2009 | Peters et al. | |
| 7,485,761 B2 | 2/2009 | Schindler et al. | |
| 8,124,572 B2 | 2/2012 | Miller | |
| 8,395,007 B2 | 3/2013 | Wright et al. | |
| 8,999,013 B2 | 4/2015 | Xu et al. | |
| 9,187,388 B2 | 11/2015 | Arjah et al. | |
| 9,605,226 B2 * | 3/2017 | Xu | C10L 1/125 |
| 9,611,192 B2 | 4/2017 | Digiulio | |
| 10,774,020 B2 | 9/2020 | Di Girolamo et al. | |
| 2002/0169346 A1 | 11/2002 | Commereuc et al. | |
| 2003/0158429 A1 | 8/2003 | Albiez et al. | |
| 2004/0171891 A1 | 9/2004 | Scholz et al. | |
| 2005/0288534 A1 | 12/2005 | Fernandez et al. | |
| 2006/0122444 A1 * | 6/2006 | Peters | C07C 2/28 |
| | | | 585/326 |
| 2007/0149839 A1 | 6/2007 | Rix et al. | |
| 2007/0265483 A1 | 11/2007 | Himelfarb | |
| 2008/0146858 A1 | 6/2008 | Elomari et al. | |
| 2008/0312481 A1 | 12/2008 | Leyshon | |
| 2009/0193710 A1 | 8/2009 | Xiong et al. | |
| 2011/0040133 A1 | 2/2011 | Vermeiren et al. | |
| 2011/0230632 A1 | 9/2011 | Abhari | |
| 2012/0117862 A1 | 5/2012 | Xu | |
| 2012/0283492 A1 | 11/2012 | Dalemat et al. | |
| 2013/0072732 A1 | 3/2013 | Breuil et al. | |
| 2013/0104449 A1 | 5/2013 | Xu et al. | |
| 2013/0172627 A1 | 7/2013 | Chewter et al. | |
| 2013/0331620 A1 | 12/2013 | Abhari | |
| 2014/0039226 A1 | 2/2014 | Xu et al. | |
| 2014/0142350 A1 | 5/2014 | Weiner et al. | |
| 2015/0225320 A1 | 8/2015 | Shaik et al. | |
| 2015/0322181 A1 | 11/2015 | Kim et al. | |
| 2016/0326079 A1 | 11/2016 | Lee et al. | |
| 2017/0073289 A1 | 3/2017 | Leal et al. | |
| 2017/0198231 A1 | 7/2017 | Xu et al. | |
| 2017/0253540 A1 | 9/2017 | Hofel et al. | |
| 2020/0157450 A1 | 5/2020 | Leal et al. | |
| 2021/0002185 A1 | 1/2021 | Leal et al. | |
| 2021/0024837 A1 | 1/2021 | Leal et al. | |
| 2021/0024843 A1 | 1/2021 | Leal et al. | |
| 2021/0214290 A1 | 7/2021 | Ansari et al. | |
| 2021/0246088 A1 | 8/2021 | Leal et al. | |

FOREIGN PATENT DOCUMENTS

| | | | |
|---|---|---|---|
| CN | 1506344 A | 6/2004 | |
| CN | 1736589 A | 2/2006 | |
| CN | 101279879 A | 10/2008 | |
| CN | 101289368 A | 10/2008 | |
| CN | 102070391 A | 5/2011 | |
| CN | 105585411 A | 5/2016 | |
| CN | 106608791 A | 5/2017 | |
| CN | 102372573 A | 3/2021 | |
| EP | 0063813 B1 | 11/1982 | |
| EP | 0102840 B1 | 3/1984 | |
| EP | 0253679 | 1/1988 | |
| EP | 0605822 A1 | 7/1994 | |
| EP | 2062865 A1 * | 5/2009 | C07C 11/04 |
| GB | 1374368 | 11/1974 | |
| JP | S5920232 A | 2/1984 | |
| JP | 2010111596 A | 5/2010 | |
| RU | 2470905 C1 | 12/2012 | |
| WO | 9011268 | 10/1990 | |
| WO | 9732838 A1 | 9/1997 | |
| WO | 0043336 A1 | 7/2000 | |
| WO | 0146095 A1 | 6/2001 | |
| WO | 2006113191 A2 | 10/2006 | |
| WO | 2007024733 A2 | 3/2007 | |
| WO | 2012095744 A2 | 7/2012 | |
| WO | 2014153570 A2 | 9/2014 | |
| WO | 2014160825 A1 | 10/2014 | |
| WO | 2015089005 A1 | 6/2015 | |
| WO | 2015123026 A1 | 8/2015 | |
| WO | 2019207477 A1 | 10/2019 | |

OTHER PUBLICATIONS

International Search Report for International Application No. PCT/IB2019/052177; International Filing Date Mar. 18, 2019; dated Jun. 26, 2019; 3 pages.

International Search Report for International Application No. PCT/IB2019/052178; International Filing Date Mar. 18, 2019; dated Jun. 26, 2019; 6 pages.

International Search Report for International Application No. PCT/IB2019/053697; International Filing Date May 6, 2019; dated Aug. 28, 2019; 11 pages.

International Search Report for International Application No. PCT/IB2019/057784; International Filing Date Sep. 16, 2019; dated Jan. 7, 2020; 5 pages.

International Search Report for International Application No. PCT/IB2019/059984; International Filing Date Nov. 20, 2019; dated Feb. 21, 2020; 5 pages.

International Search Report for International Application No. PCT/US2019/026985; International Filing Date Apr. 11, 2019; dated May 27, 2019; 6 pages.

International Search Report for International Application No. PCT/US2019/028092; International Filing Date Apr. 18, 2019; dated Jun. 26, 2019; 6 pages.

International Search Report for International Application No. PCT/US2019/028099; International Filing Date Apr. 18, 2019; dated Jun. 26, 2019; 6 pages.

International Search Report; International Application No. PCT/IB2018/055647; International Filing Date: Jul. 27, 2018; dated Oct. 30, 2018; 6 pages.

Izquierdo et al.; "Equilibrium Constants for Methyl tert-Butyl Ether Liquid-Phas Synthesis"; J. Chem. Eng. Data, vol. 37; 1992; pp. 339-343.

Kalamaras et al.; "SuperButol—A novel high-octane gasoline blending component"; Fuel, vol. 195; 2017; pp. 165-173.

Leal et al. U.S. Appl. No. 17/045,669, entitled "Method of Producing a Fuel Additive", filed with the USPTO on Oct. 6, 2020.

Leal et al. U.S. Appl. No. 17/052,407, entitled "Method of Producing a Fuel Additive", filed with the USPTO on Nov. 2, 2020.

Written Opinion for International Application No. PCT/IB2019/052177; International Filing Date Mar. 18, 2019; dated Jun. 26, 2019; 9 pages.

Written Opinion for International Application No. PCT/IB2019/052178; International Filing Date Mar. 18, 2019; dated Jun. 26, 2019; 9 pages.

Written Opinion for International Application No. PCT/IB2019/053697; International Filing Date May 6, 2019; dated Aug. 28, 2019; 9 pages.

Written Opinion for International Application No. PCT/IB2019/057784; International Filing Date Sep. 16, 2019; dated Jan. 7, 2020; 7 pages.

Written Opinion for International Application No. PCT/IB2019/059984; International Filing Date Nov. 20, 2019; dated Feb. 21, 2020; 8 pages.

Written Opinion for International Application No. PCT/US2019/026985; International Filing Date Apr. 11, 2019; dated May 27, 2019; 7 pages.

Written Opinion for International Application No. PCT/US2019/028092; International Filing Date Apr. 18, 2019; dated Jun. 26, 2019; 9 pages.

Written Opinion for International Application No. PCT/US2019/028099; International Filing Date Apr. 18, 2019; dated Jun. 26, 2019; 13 pages.

(56) References Cited

OTHER PUBLICATIONS

Written Opinion; International Application No. PCT/IB2018/055647; International Filing Date: Jul. 27, 2018; dated Oct. 30, 2018; 11 pages.
International Search Report for International Application No. PCT/IB2020/051908; International Filing Date Mar. 5, 2020; dated May 29, 2020; 6 pages.
Leal et al. U.S. Appl. No. 17/436,753, entitled "Method of Producing a Fuel Additive", filed with the USPTO on Sep. 7, 2021.
Written Opinion for International Application No. PCT/IB2020/051908; International Filing Date Mar. 5, 2020; dated May 29, 2020; 9 pages.
Streich et al.; "Secure the Best Benefits from C4 Hydrocarbon Processing—Part 1: Separation Sequences"; Hydrocarbon Processing: Process Engineering and Optimization; 2016; 6 pages.

* cited by examiner

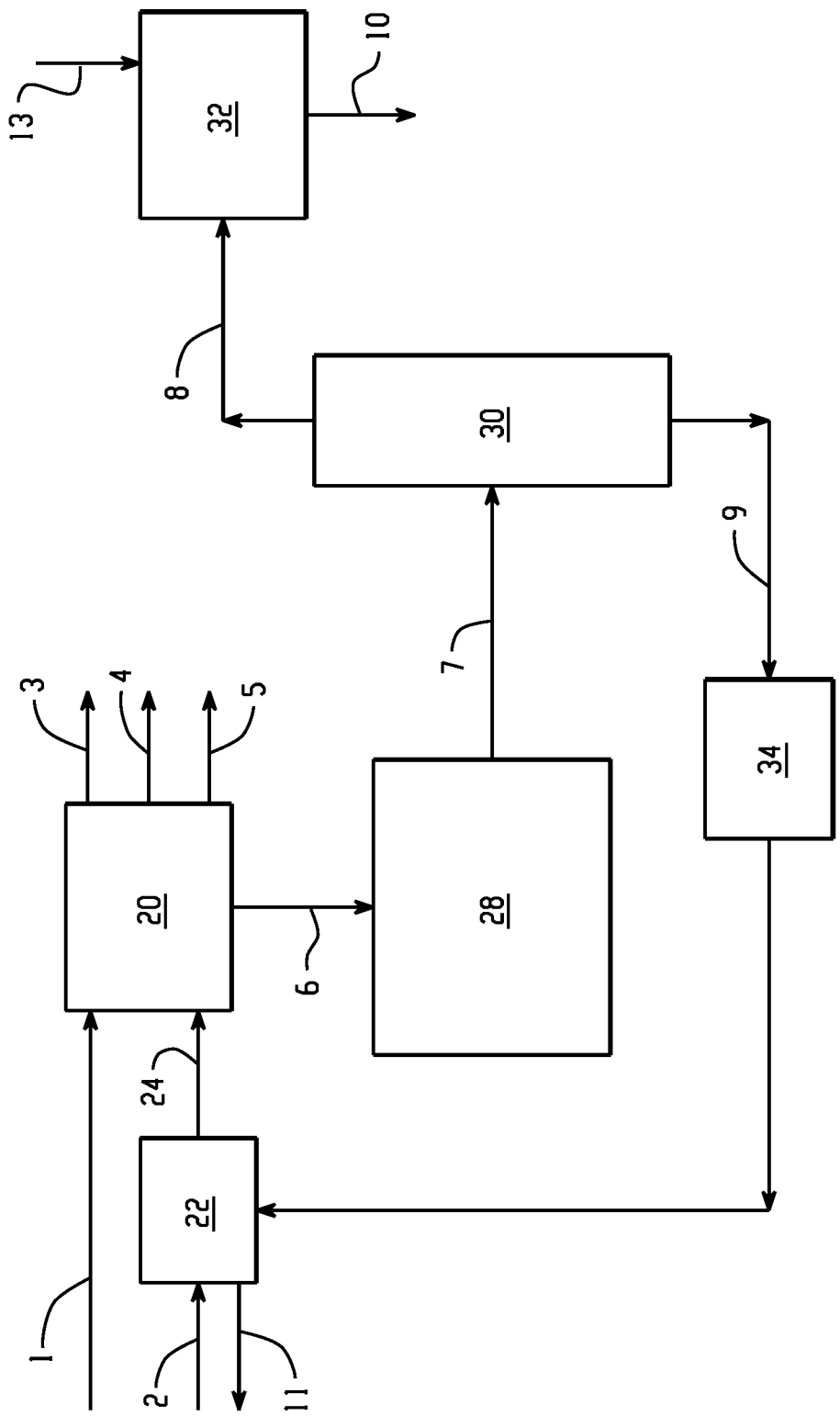

PROCESS AND SYSTEM FOR PRODUCING ETHYLENE AND AT LEAST ONE OF BUTANOL AND AN ALKYL TERT-BUTYL ETHER

CROSS REFERENCE TO RELATED APPLICATIONS

This application is a National Stage application of PCT/IB2019/059984, filed Nov. 20, 2019, which claims the benefit of U.S. Provisional Application No. 62/769,864, filed Nov. 20, 2018, both of which are incorporated by reference in their entireties herein.

BACKGROUND

Commercial gasoline, which is fuel for internal combustion engines, is a refined petroleum product that is typically a mixture of hydrocarbons (base gasoline), additives, and blending agents. Additives and blending agents are added to the base gasoline to enhance the performance and the stability of gasoline, and can include anti-knock agents, anti-oxidants, metal deactivators, lead scavengers, anti-rust agents, anti-icing agents, upper-cylinder lubricants, detergents, and dyes.

When used in high compression internal combustion engines, gasoline has the tendency to "knock." Knocking occurs when combustion of the air/fuel mixture in the cylinder does not start off correctly in response to ignition because one or more pockets of air/fuel mixture pre-ignite outside the envelope of the normal combustion front. Anti-knocking agents, also known as octane boosters, reduce the engine knocking phenomenon, and increase the octane rating of the gasoline. Prior octane boosters such as tetraethyl lead and methylcyclopentadienyl manganese tricarbonyl ("MMT") have been or are being phased out for environmental, health, or other reasons.

Methyl tert-butyl ether ("MTBE") is an aliphatic alkyl ether that is used as a gasoline additive to increase the octane rating of gasoline products. Typically, MTBE is produced on a large scale by reaction of isobutene with methanol according to the reaction (I)

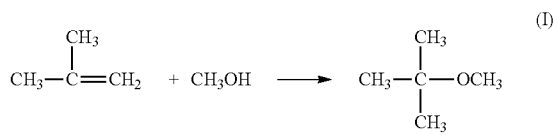

One major challenge in refinery and petrochemical arts is to achieve the required purity and volume to match the commercial targets of different products, such as fuel additives.

In the case of a mixed C4 hydrocarbons stream, which can be a recycle stream from a cracker such as a steam cracker, the components of the stream can be valuable and can include components such as n-butane, 1-butene, 2-butene, and isobutene. The separation of each of these components presents a technical and financial challenge. The utilization of isobutene, n-butane, 1-butene, and 2-butene individually from the recycle stream of a steam cracker can increase the financial benefits of the original mixed C4 stream from the cracker.

In view of the foregoing, there remains a need to provide a cost-effective process of increasing the capacity of MTBE production plants and increased cracker feed handling capability in order to efficiently and cost effectively produce products, e.g., fuel additive products, such as alcohols, methyl-tert butyl ether, and butenes.

SUMMARY

Disclosed, in various embodiments, are a process and system for producing ethylene and at least one of butanol and an alkyl tert-butyl ether.

A process for producing ethylene and at least one of butanol and an alkyl tert-butyl ether from field butane comprises: separating the field butane into an n-butane stream and an isobutane stream; cracking the n-butane stream to obtain a cracked product stream comprising n-butane, 1-butene, 2-butene, butadienes, or a combination comprising at least one of the foregoing; and at least one of the following: (1) separating the cracked product stream to obtain a butane stream and a butene stream, and reacting the butene stream with water to obtain a fuel additive comprising butanol; and (2) dehydrogenating the isobutane stream in a dehydrogenation unit to form an isobutene stream and reacting the isobutene stream with an aliphatic alcohol to produce an alkyl tert-butyl ether.

A system for producing ethylene and at least one of butanol and an alkyl tert-butyl ether from field butane comprises: an n-butanizer unit for separating the field butane into an n-butane stream and an isobutane stream; a cracker for cracking the n-butane stream to obtain a cracked product stream comprising butane, n-butane, 1-butene, 2-butene, and butadienes; and at least one of the following: (1) a separation unit for separating the cracked product stream to obtain a butane stream and a butene stream, and a hydration unit for reacting the butene stream with water to obtain butanol; and (2) a dehydrogenation unit for dehydrogenating the isobutane stream to an isobutene stream and an ether synthesis unit for reacting the isobutene stream with an aliphatic alcohol to produce an alkyl tert-butyl ether.

These and other features and characteristics are more particularly described below.

BRIEF DESCRIPTION OF THE DRAWING

The following is a brief description of the drawing wherein like elements are numbered alike and which is presented for the purposes of illustrating the exemplary embodiments disclosed herein and not for the purposes of limiting the same.

FIG. is a schematic diagram of the process and system disclosed herein.

These and other features and characteristics are more particularly described below.

DETAILED DESCRIPTION

Disclosed herein in various embodiments, are a process and system for producing ethylene and at least one of butanol and an alkyl tert-butyl ether. The system integrates several production processes and has several surprising advantageous features, including a reduction in column size due to recycling of n-butane to an n-butanizer column instead of to a cracker. Another advantageous feature is in allowing an MTBE plant to be supplied with isobutane directly, instead of supplying n-butane to an isomerization unit to produce isobutane, which is then passed to a dehydrogenation unit and then to an MTBE synthesis unit. The process results in an increased capacity of the MTBE production plant and increased cracker feed handling capability.

In the present process, isobutane is partly separated from field butane by an n-butanizer unit and is then sent to a dehydrogenation unit in the overall synthesis of MTBE. Field butane is a product that primarily includes n-butane or a mixture of n-butane and isobutane. Typically, field butane is obtained from gas oil separation plants. Gas oil separation plants typically include a sulfur removal system and a depropanizer unit. The field butane is supplied from the gas oil separation plants as piped liquid at room temperature and at a pressure above that required to maintain the butane in liquid phase. In the present process, the n-butanizer unit separates and/or converts the field butane into pure n-butane for cracking. The separation unit of this n-butanizing process includes a de-isobutanizer to convert isobutane to pure n-butane for cracking, e.g., steam cracking.

The cracking process contemplated herein is not particularly limited and can be performed in accordance with known cracking processes used in the petrochemical arts, including steam cracking. Generally, steam cracking is a process by which saturated hydrocarbons are broken down into smaller, often unsaturated, hydrocarbons. Steam cracking results in the conversion of heavier materials into lower molecular weight products that can be separated into streams of similar sized hydrocarbons. For instance, steam cracking may be used to produce a $C_4$ stream containing a mixture of different $C_4$ species, including n-butane, isobutane, isomeric butenes (e.g. 1-butene, cis- and trans-2-butene, and isobutene), and 1,3-butadiene. In addition, such $C_4$ streams may contain one or more other chemical species, non-limiting examples of which include ethyl acetylene, dimethyl acetylene, vinyl acetylene, and diacetylene. The products obtained depend on the composition of the feed, the hydrocarbon-to-steam ratio, and on the cracking temperature and furnace residence time.

The process disclosed herein can make use of field butane streams and produce final products with low impurities and high performance specifications. For example, product specifications for final products ethylene, MTBE, and SUPERBUTOL™ are listed in Tables 1 to 3.

TABLE 1

Ethylene Product Specifications

| Characteristic | Unit | Specification | Test Method |
| --- | --- | --- | --- |
| Purity * | vol % | 99.9 min. | ASTM D-2505 |
| Methane + ethane | ppm, vol | 1000 max. | ASTM D-2505 |
| $C_3 + C_4$ | ppm, vol | 10 max. | ASTM D-2505 |
| Ethane | ppm, vol | 500 max. | ASTM D-2505 |
| Acetylene | ppm, vol | 5 max. | ASTM D-2505 |
| Hydrogen | ppm, vol | 5 max. | ASTM D-2504 |
| Oxygen | ppm, vol | 5 max. | — |
| Carbon monoxide | ppm, vol | 2 max. | ASTM D-2505 |
| Acetone + Methane + n-propanol | ppm, wt | 10 max. | ASTM D-4815 |
| Carbon dioxide | ppm, vol | 5 max. | ASTM D-2505 |
| Water | ppm, wt | 5 max. | ASTM D-1142 |
| Total Sulfur (as S) | ppm, wt | 1 max. | ASTM D-4045 |
| Total basic nitrogen (Calculated as $NH_3$) | ppm, vol | 5 max. | ASTM D-4629 |

TABLE 2

MTBE Product Specifications

| Characteristic | Unit | Specification | Test Method |
| --- | --- | --- | --- |
| Purity | wt % | 98 min | ASTM D-5441 |
| $C_4$-hydrocarbons | wt % | 0.5 max | ASTM D-5441 |
| $C_5$-hydrocarbons | wt % | 1 max | ASTM D-5441 |
| Methanol | wt % | 0.7 max | ASTM D-5441 |
| Ter-butyl alcohol | wt % | 0.6 max | ASTM D-5441 |
| Di-isobutene | wt % | 0.6 max | ASTM D-5441 |
| Water | ppm | 500 max | ASTM D-1364 |

TABLE 3

SUPERBUTOL ™ Product Specifications

| Characteristic | Unit | Specification | Test Method |
| --- | --- | --- | --- |
| 2-Butanol | wt % | 50 min | ASTM D-5441 |
| Tert-Butanol | wt % | 30 max | ASTM D-5441 |
| $C_4$-hydrocarbons | wt % | 0.5 max | ASTM D-5441 |
| $C_8$-hydrocarbons | wt % | 15 max | ASTM D-5441 |
| Di-Sec-butyl Ether | wt % | 5 max | ASTM D-5441 |
| Water | ppm | 500 max | ASTM D-1364 |

For example, the process disclosed herein can provide a sequence of operations that converts the field butane into valuable fuel additives, such as alcohol fuel additives (e.g., C4 alcohols and butanols), MTBE, and ethylene. The process can reduce total capital costs by converting impurities to the process in the feedstream such as alkanes and butadienes to valuable products, e.g., fuel additive products. This is compared to a conventional process, which does not convert these impurities in the feedstream into valuable products. For example, the presence of alkanes and butadienes in the feedstream of a conventional process can be poisonous and can prevent reactions from occurring. The advantageous processes disclosed herein can produce final products comprising 2-butanol, tert-butyl alcohol, ethers, C4-dimers, or a combination comprising at least one of the foregoing. The final products can have high octane numbers (e.g., greater than or equal to 85 Research Octane Number ("RON"), or greater than or equal to 87 RON), and the final products can have low Reid vapor pressures of less than or equal to 55 KiloPascals (8.0 pounds per square inch (psi)). Any one or all of these properties can correlate with high performance and high market value.

The field butane can comprise n-butane in an amount of 50 mole % to 80 mole %, preferably 55 mole % to 75 mole %, more preferably 60 mole % to 75 mole %, based on the total moles of the field butane; and the field butane can comprise isobutane in an amount of 10 mole % to 50 mole %, preferably 15 mole % to 45 mole %, more preferably 20 mole % to 40 mole %, based on the total moles of the field butane. The field butane can further comprise 0 mole % to 5 mole % propane, preferably 1 mole % to 4 mole %, more preferably 2 mole % to 3 mole %. The field butane can further comprise 0 mole % to 2.5 mole % isopentane (e.g., greater than 0 mole % to 2.5 mole %), and 0 mole % to 1.5 mole % n-pentane, preferably 0.5 mole % to 1.0 mole %. The n-butane/isobutane molar ratio in the field butane can be 1.8 to 2.8. The field butane can comprise 94 mole % to 98 mole % n-butane and isobutane collectively.

For processes in which hydrocarbons are to be cracked, a high linear hydrocarbon/branched hydrocarbon ratio is preferred. Processes of increasing the ratio of linear butane/branched butane in field butane are described in U.S. application No. 62/663,845, which is herein incorporated by reference in its entirety. With the increase of this ratio, the utilization efficiency of field butane as feedstock in thermal cracking units can be improved.

The process of increasing the ratio of linear butane/branched butane in field butane can include subjecting a field butane feedstream comprising n-butane and isobutane to a concentrating process, where the concentrating process includes distilling the field butane feedstream in one or more distillation columns within an n-butanizer unit. The concentrating process assists in increasing the ratio of linear butane/branched butane in a field butane feedstream.

In the n-butanizer unit, the field butane feedstream can be distilled to produce a bottoms stream, which can comprise primarily n-pentane, an intermediate stream, which can comprise primarily n-butane, and an overhead stream, which can comprise primarily isobutane. The intermediate stream can comprise n-butane in an amount equal to or greater than 85 mole %, preferably equal to or greater than 93 mole %, more preferably equal to or greater than 95 mole %, even more preferably 100 mole %, based on the total moles of the intermediate stream. For example, the intermediate stream can comprise 96 mole % to 100 mole % n-butane, based on the total moles of the intermediate stream. The overhead stream can comprise isobutane in an amount equal to or greater than 85 mole %, preferably equal to or greater than 93 mole %, more preferably equal to or greater than 95 mole %, based on the total moles of the overhead stream. For example, the overhead stream can comprise 94 mole % to 98 mole % isobutane and 2 mole % to 6 mole % propane, based on the total moles of the overhead stream; the intermediate stream can comprise 96 mole % to 100 mole % n-butane, based on the total moles of the intermediate stream; and the bottoms stream can comprise 96 mole % to 100 mole % n-pentane, based on the total moles of the bottoms stream.

In some embodiments, the overhead stream can be isomerized in an isomerization reactor to convert at least some of the isobutane to n-butane. The isomerizing includes mixing the overhead stream with hydrogen and contacting this mixture with a catalyst under reaction conditions sufficient to isomerize at least some of the isobutane to n-butane. The catalyst used in isomerizing the isobutane can include, but is not limited to, sulfated zirconia, platinum on alumina, platinum on alumina dosed with perchloroethylene or other chlorinating agent, fluidized catalyst, or a combination comprising at least one of the foregoing. In some embodiments, the catalyst used does not contain zeolite because zeolite can favor formation of branched hydrocarbons. The reaction conditions for the isomerization process in the reactor can include a reaction temperature of 130 to 300° C., a pressure of 10 to 30 bar (1 megaPascal (mPa) to 3 mPa) and a gas hourly space velocity (GHSV) of 4.0 to 5.5. An effluent from the reactor comprises 42 mole % to 52 mole % isobutane and 35 mole % to 45 mole % n-butane.

The intermediate stream can be combined with the bottoms stream to produce the first product stream. The first product stream can comprise 85 mole % to 95 mole % n-butane. The first product stream can also include n-pentane, methane, ethane, and/or propane.

The first product stream can be sent to a cracker, such as a steam cracker. In the cracker, the first product stream can be cracked to produce a first cracked stream comprising primarily ethylene; a second cracked stream, comprising primarily propylene; a third cracked stream, comprising primarily benzene; and a fourth cracked stream, comprising n-butane and also containing 1-butene, 2-butene, butadienes such as 1,3-butadiene, as well as other components, which may include ethyl acetylene, dimethyl acetylene, vinyl acetylene, and/or diacetylene.

The fourth cracked stream can then be sent to a hydrogenation unit, such as a selective hydrogenation unit. In the selective hydrogenation unit, the 1,3-butadiene in the fourth cracked stream is converted to 1-butene and 2-butene in the presence of a catalyst. The hydrogenation catalyst can comprise palladium with an aluminum base. The hydrogenation catalyst can comprise platinum, rhodium, palladium, ruthenium, cobalt, nickel, copper, or a combination comprising at least one of the foregoing.

The hydrogenated stream from the selective hydrogenation unit is then sent to an olefins separation unit. In the olefins separation unit, the hydrogenated stream is separated into a butene stream, comprising primarily 1-butene and 2-butene; and a butane stream, which can comprise n-butane and isobutane.

The butene stream is then sent to a hydration unit, in which it is reacted with water in the presence of a hydration catalyst such as a cation exchange resin to produce a fuel additive comprising butanol.

It is noted that butadienes such as 1,3-butadiene can negatively impact the effectiveness of the cationic ion-exchange resin used to catalyze the production of a fuel additive in the hydration unit. By converting the butadienes to 1-butene and 2-butene in the selective hydrogenation unit, this adverse result can be avoided.

Another problem can be that a high level of inert materials (e.g., alkanes) can cause excessive purge, thereby leading to losses of efficiency in the hydration unit because the inert materials occupy space in the hydration unit that might otherwise be occupied by olefins that can react to form the fuel additive. In addition, high quantities of inert materials in the hydration unit can contribute to excessive utility consumption. By separating the hydrogenated stream into a butene stream and a butane stream, and sending only the butene stream to the hydration unit, the above-described problems can be avoided.

The butane stream from the olefins separation unit is then recycled to the n-butanizer unit. From the n-butanizer unit, the isobutane present in the butane stream can be sent to a dehydrogenation unit to produce isobutene, which is then sent to an ether synthesis unit in which the isobutene is reacted with methanol in the presence of a catalyst such as a cationic ion exchange resin to produce an alkyl tert-butyl ether such as methyl tert-butyl ether (MTBE).

The chemical reaction used to produce MTBE is not particularly limited, and can be a reaction that is compatible with the isobutene-containing feedstream from the steam cracker unit. In certain embodiments, the chemical reaction used to produce MTBE is a liquid phase reaction of isobutene and methanol catalyzed by cationic ion-exchange resin (see, e.g., Izquierdo, J. F., Cunill, F., Vila M., Tejero J. and Tborra M. Equilibrium constants for methyl tertiary butyl ether liquid-phase synthesis. Journal of Chemical and Engineering Data, 1992, vol. 37, p. 339; Brockwell, H. L., Sarathy P. R. and Trotta R. Synthesize ethers. Hydrocarbon Processing, 1991, vol. 70, No. 9, p. 133; Chemical Economics Handbook, Gasoline Octane Improvers. CEH Marketing Report, 1986, p. 543, Stanford Research Institute, SRI International, Menlo Park, CA).

A more complete understanding of the components, processes, and apparatuses disclosed herein can be obtained by reference to the accompanying drawing. This FIGURE (also referred to herein as "FIG.") is merely a schematic representation based on convenience and the ease of demonstrating the present disclosure, and is, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawing, and are not intended to define or limit the scope of the disclosure. In the drawing and the following description below, it is to be understood that like numeric designations refer to components of like function.

A system and process for producing ethylene and at least one of butanol and an alkyl tert-butyl ether from field butane as disclosed herein can include the following features shown in the FIGURE.

A feedstream 1 comprising ethane is fed to a cracker unit 20, for example a steam cracker unit 20. In addition, a field butane stream 2 is passed through an n-butanizer unit 22. In the n-butanizer unit 22, the field butane stream 2 is concentrated via distillation to produce a first product stream 24, containing primarily n-butane, and an isobutane stream 11, which can be sent to a dehydrogenation unit (not shown) and then to an ether synthesis unit (not shown) via isobutane stream 11. The first product stream 24 is passed to the cracker unit 20. In the cracker unit 20, the first product stream 24 is cracked along with the ethane in feedstream 1 to obtain a first cracked stream 3 comprising ethylene, a second cracked stream 4 comprising propylene, a third cracked stream 5 comprising benzene, and a fourth cracked stream 6 comprising n-butane, 1-butene, 2-butene, butadienes (e.g., 1,3-butadienes), or a combination comprising at least one of the foregoing.

The fourth cracked stream 6 is sent to a hydrogenation unit 28 (e.g., a selective hydrogenation unit 28), where the fourth cracked stream 6 is contacted with a hydrogenation catalyst. The hydrogenation catalyst can comprise palladium with an aluminum base, platinum, rhodium, palladium, ruthenium, cobalt, nickel, copper, or a combination comprising at least one of the foregoing, or another Group VIII metal. The hydrogenation unit 28 converts butadiene components present in the fourth cracked stream 6 into 1-butene and 2-butene. The hydrogenated stream 7 emanating from the hydrogenation unit 28 comprises butane as well as 1-butene and 2-butene, among other components. A high level of inert materials (e.g., 3% to 60% wt %, or 5% to 50% wt %, or 3% to 5% wt % inert materials, such as alkanes) can be present in the hydrogenated stream 7. Such a high level can cause excessive purge, leading to losses of efficiency in hydration unit 32, so hydrogenated stream 7 is passed through an olefins separation unit 30 to be separated into alkanes and olefins prior to hydration unit 32. A butene stream 8 comprising 1-butene and 2-butene exits the olefins separation unit 30 and is sent to hydration unit 32.

In the hydration unit 32, the butene stream 8 is reacted with water via water stream 13 to obtain a fuel additive product stream 10 comprising butanol. A recycled butane stream 9 exits the olefins separation unit 30 and is recycled to the n-butanizer unit 22. The recycled butane stream 9 may optionally be passed through an optional activated carbon trap 34 before entering the n-butanizer unit 22. The activated carbon trap 34 can assist in isolating extraneous solvent impurities that may enter the system via a non-distillation separation process in the event such is chosen for the olefins separation unit 30. From n-butanizer unit 22, the isobutane from recycled butane stream 9 can be sent via isobutane stream 11 to a dehydrogenation unit (not shown), in which the isobutane is dehydrogenated into isobutene, and then to an ether synthesis unit (not shown), in which it can be reacted with an alcohol such as methanol to produce an alky tert-butyl ether, for example, MTBE.

The fuel additive product stream 10 can comprise butanol (e.g., 2-butanol), tert-butyl alcohol, di-isobutene, C4-dimers, or a combination comprising at least one of the foregoing. For example, the C4-dimers can comprise di-isobutylene, 2,2,4 trimethyl-pentane, 2,3,3 trimethyl-pentane, or a combination comprising at least one of the foregoing. The fuel additive product stream 10 can comprise greater than or equal to 0.01 wt % trimethyl-pentane. For example, the fuel additive product stream 10 can comprise greater than or equal to 5 wt % trimethyl-pentane, for example, greater than or equal to 10 wt % trimethyl-pentane, for example, greater than or equal to 15 wt % trimethyl-pentane, greater than or equal to 20 wt % trimethyl-pentane, for example, greater than or equal to 50 wt % trimethyl-pentane. The fuel additive product stream 10 can comprise greater than or equal to 0.01 wt % to 50 wt % trimethyl-pentane. An octane number of the fuel additive product stream 10 can be greater than or equal to 80 according to the Anti-Knock Index, for example, greater than or equal to 85, for example, greater than or equal to 87, for example, greater than or equal to 90, for example, greater than or equal to 93 for example, greater than or equal to 95.

The octane number is a standard measurement used to gauge the performance of an engine or fuel. The higher the octane number, the more compression the fuel is able to withstand before igniting. Fuels with higher octane ratings are generally used in high performance gasoline engines that need higher compression ratios. Fuels with lower octane numbers can be desirable for diesel engines because diesel engines do not compress the fuel, but rather compress only air and then inject fuel into the air which is heated by compression. Gasoline engines rely on ignition of air and fuel compressed together as a mixture, which is ignited at the end of the compression stroke using spark plugs. As a result, high compressibility of fuel is a consideration for gasoline engines.

The Anti-Knock Index is measured by adding the Research Octane Number ("RON") and the Motor Octane Number ("MON") and dividing by two, e.g., (RON+MON)/2. The Research Octane Number is determined by running the fuel in a test engine at a speed of 600 revolutions per minute with a variable compression ratio under controlled conditions, and comparing the results with those for mixtures of iso-octane and n-heptane. Motor Octane Number is determined by testing a similar test engine to that used in determining the Research Octane Number but at a speed of 900 revolutions per minute with a preheated fuel mixture, higher engine speed, and variable ignition timing. Depending on the composition, the Motor Octane Number can be about 8 to 12 octanes lower than the Research Octane Number. The Research Octane Number can be greater than or equal to 88, for example, greater than or equal to 91, for example, greater than or equal to 93, greater than equal 95, greater than equal to 100. The Motor Octane Number can be greater than or equal to 82, for example, greater than or equal to 89, for example, greater than or equal to 90, for example, greater than or equal to 93. Higher octane ratings can give higher amounts of energy needed to initiate combustion. Fuels with higher octane ratings are less prone to auto-ignition and can withstand a greater rise in temperature during the compression stroke of an internal combustion engine without auto-igniting.

Reid vapor pressure is used to measure the volatility of gasoline defined as the absolute vapor pressure exerted by a liquid at 37.8° C. as determined by the test method ASTM D-323, which measures the vapor pressure of gasoline, volatile crude oil, and other volatile petroleum products, except for liquefied petroleum gases. Reid vapor pressure is measured in Kilopascals and represents a relative pressure to atmospheric pressure since ASTM D-323 measures the gauge pressure of the sample in a non-evacuated chamber. High levels of vaporization are desired for winter starting and operation and lower levels are desirable in avoiding vapor lock during summer heat. Fuel generally cannot be pumped when vapor is present in the fuel line, and winter starting can be difficult when liquid gasoline in the combustion chambers has not vaporized. This means that the Reid vapor pressure is changed accordingly by oil producers seasonally to maintain gasoline engine reliability.

The Reid vapor pressure of the product stream 10 can be less than or equal to 55.16 kiloPascals, for example, 5 kiloPascals to 55 kiloPascals, for example, 5 kiloPascals to 40 kiloPascals. The Reid vapor pressure can vary during winter and summer conditions such that the pressure can be at the higher end of the values during the winter and at the lower end of the values during the summer.

EXAMPLE

Example 1

In the following example, an exemplary process to create the butanol products disclosed herein was completed. The streams listed in Table 4 correspond to the streams in the FIGURE. The tons per hour output ("T/H") of each stream is shown. The field butane stream 2 and the first cracked product stream 3 (comprising ethylene) produced the most output per hour.

TABLE 4

Output of Streams

| | Stream # | T/H |
|---|---|---|
| Ethane | 1 | 75.598 |
| Isobutane to Dehydrogenation unit of MTBE | 11 | 34.870 |
| Field Butane Stream | 2 | 358.926 |
| Ethylene | 3 | 207.294 |
| Propylene | 4 | 81.572 |
| Benzene | 5 | 12.790 |
| before selective hydrogenation unit (fourth cracked product stream) | 6 | 51.660 |
| After selective hydrogenation unit (hydrogenated stream) | 7 | 52.07 |
| Butene stream | 8 | 13.07 |
| Butane recycle stream | 9 | 34.87 |
| Fuel Additive product stream | 10 | 17.27 |

Table 5 lists the composition for the field butane stream 2, Table 6 lists the composition for the fourth cracked stream 6, Table 7 lists the composition for hydrogenated stream 7, Table 8 lists the composition for butane recycle stream 9, and Table 9 lists the composition for butene stream 8.

TABLE 5

Composition Stream #2

| Components | wt % |
|---|---|
| $C_3H_8$ | 2.62 |
| isobutane | 28.87 |
| n-butane | 67.70 |

TABLE 5-continued

Composition Stream #2

| Components | wt % |
|---|---|
| isopentane | 0.00 |
| n-pentane | 0.80 |

TABLE 6

Composition Stream #6

| Components | wt % |
|---|---|
| $C_4H_6$ | 21.07 |
| 1-$C_4H_8$ | 8.43 |
| 2-$C_4H_8$ | 5.18 |
| iso-$C_4H_8$ | 0.00 |
| $nC_4H_{10}$ | 65.31 |

TABLE 7

Composition Stream #7

| Components | wt % |
|---|---|
| n-$C_4H_{10}$ | 66.97 |
| i-$C_4H_{10}$ | 0.00 |
| n-$C_5H_{12}$ | 0.00 |
| 1-$C_4H_8$ | 22.03 |
| 2-$C_4H_8$ | 3.08 |

TABLE 8

Composition Stream #9

| Components | wt % |
|---|---|
| n-$C_4H_{10}$ | 99.19 |
| i$C_4H_{10}$ | 0.00 |
| n-$C_5H_{12}$ | 0.81 |
| iso$C_5H_{12}$ | 0.00 |

TABLE 9

Composition Stream #8

| Components | wt % |
|---|---|
| 1-$C_4H_8$ | 87.74 |
| 2-$C_4H_8$ | 12.26 |

A base case field butane, an n-butanized cracker feed, and an n-butanized cracker feed plus butanol as disclosed herein along with their outputs measured in kilotons per annum ("KTA") are displayed in Table 10. Table 10 also lists the tons per hour (T/H) and KTA for stream 1: ethane; and for stream 2: field butane; and for methanol, which was used as feed in the MTBE synthesis unit.

TABLE 10

Product Slate and Feed Composition Basis

| Components | Base Case Field butane KTA | n-Butanized Cracker Feed* KTA | n-butanized cracker feed + butanol, propene constant KTA | Delta KTA |
|---|---|---|---|---|
| Ethylene | 1527.85 | 1656.95 | | 129.0995 |
| Propylene | 663.37 | 652.62 | | −10.7492 |
| 1,3 butadiene | 0.00 | 0.00 | | 0 |
| 1-butene | 0.00 | 0.00 | | 0 |
| Benzene | 118.45 | 102.33 | | −16.1104 |
| Butanol | 0.00 | 0.00 | 138.17 | 138.1739 |
| MTBE | | | 364.40 | 364.3989 |

Feed for cracker and MTBE synthesis unit

| Components | T/H | T/H | T/H | KTA |
|---|---|---|---|---|
| Ethane (Stream 1) | 75.598 | 75.598 | 75.60 | 0 |
| Field Butane (Stream 2) | 305.188 | 358.930 | 358.93 | 429.906 |
| Methanol | | 16.443 | | 131.548 |

*propylene output is kept constant by increasing field butane feed

As can be seen in Table 10, ethylene, butanol and MTBE production were increased by 129 KTA, 138 KTA and 364 KTA, respectively, with a minor decrease in propylene and benzene production (10 KTA and 16 KTA, respectively).

Table 11 lists a comparison of the field butane stream 2 (labeled "Field Butane Stream") and the first product stream 24 (labeled "n-butanized").

TABLE 11

Field Butane Stream and n-butanized streams compared

| Components | Field Butane Stream wt % | n-butanized wt % |
|---|---|---|
| CH$_4$ | | 0.20 |
| C$_2$H$_6$ | | 0.74 |
| C$_3$H$_8$ | 2.62 | 3.75 |
| isobutane | 28.87 | |
| n-butane | 67.70 | 94.32 |
| isopentane | 0.00 | |
| n-pentane | 0.80 | |
| Total | 100 | 100 |

As can be seen in Table 11, the first product stream 24 (e.g., n-butanized stream 24) contains nearly 30% more n-butane than the field butane stream 2.

The processes disclosed herein include at least the following aspects:

Aspect 1: A process for producing ethylene and at least one of butanol and an alkyl tert-butyl ether from field butane, comprising: separating the field butane into an n-butane stream and an isobutane stream; cracking the n-butane stream to obtain a cracked product stream comprising n-butane, 1-butene, 2-butene, butadienes, or a combination comprising at least one of the foregoing; and at least one of the following: (1) separating the cracked product stream to obtain a butane stream and a butene stream, and reacting the butene stream with water to obtain a fuel additive comprising butanol, and (2) dehydrogenating the isobutane stream in a dehydrogenation unit to form an isobutene stream and reacting the isobutene stream with an aliphatic alcohol to produce an alkyl tert-butyl ether.

Aspect 2: The process of Aspect 1, wherein the step of separating the field butane comprises distilling the field butane.

Aspect 3: The process of any one or more of the preceding aspects, wherein the field butane comprises n-butane in an amount of 50 mole % to 80 mole %, preferably, 55 mole % to 75 mole %, based on the total moles of the field butane, and isobutane in an amount of 10 mole % to 50 mole %, preferably, 15 mole % to 45 mole %, based on the total moles of the field butane.

Aspect 4: The process of Aspect 1 or Aspect 2, wherein the field butane comprises n-butane in an amount of 60 mole % to 75 mole % based on the total moles of the field butane, and isobutane in an amount of 20 mole % to 40 mole %, based on the total moles of the field butane.

Aspect 5: The process of Aspect 3 or Aspect 4, wherein the field butane further comprises greater than 0 mole % to 5 mole % propane, preferably, 1 mole % to 4 mole % propane, based on the total moles of the field butane.

Aspect 6: The process of Aspect 3 or Aspect 4, wherein the field butane further comprises 2 mole % to 3 mole % propane, based on the total moles of the field butane.

Aspect 7: The process of Aspects 3-6, wherein the field butane further comprises greater than 0 mole % to 2.5 mole % isopentane, based on the total moles of the field butane.

Aspect 8: The process of Aspects 3-7, wherein the field butane further comprises greater than 0 mole % to 1.5 mole % n-pentane, based on the total moles of the field butane.

Aspect 9: The process of Aspects 3-7, wherein the field butane further comprises 0.5 mole % to 1.0 mole % n-pentane, based on the total moles of the field butane.

Aspect 10: The process of any one or more of the preceding aspects, wherein the n-butane stream comprises n-butane in an amount equal to or greater than 85 mole %, preferably, equal to or greater than 93 mole %, based on the total moles of the n-butane stream.

Aspect 11: The process of Aspects 1-9, wherein the n-butane stream comprises n-butane in an amount equal to or greater than 95 mole %, based on the total moles of the n-butane stream.

Aspect 12: The process of Aspects 1-9, wherein the n-butane stream comprises n-butane in an amount of 100 mole %, based on the total moles of the n-butane stream.

Aspect 13: The process of any one or more of the preceding aspects, wherein the isobutane stream comprises isobutane in an amount equal to or greater than 85 mole %, based on the total moles of the isobutane stream.

Aspect 14: The process of Aspects 1-12, wherein the isobutane stream comprises isobutane in an amount equal to or greater than 93 mole %, based on the total moles of the isobutane stream.

Aspect 15: The process of Aspects 1-12, wherein the isobutane stream comprises isobutane in an amount equal to or greater than 95 mole %, based on the total moles of the isobutane stream.

Aspect 16: The process of any one or more of the preceding aspects, further comprising hydrogenating the cracked product stream with hydrogen in the presence of a hydrogenation catalyst before the step of separating the cracked product stream.

Aspect 17: The process of any one or more of the preceding aspects, further comprising recycling the butane stream to the step of separating the field butane.

Aspect 18: The process of any one or more of the preceding aspects, wherein the alkyl tert-butyl ether comprises methyl tert butyl ether, ethyl tert-butyl ether, or a combination comprising at least one of the foregoing.

Aspect 19: An ethylene product and at least one of a butanol product and an alkyl tert-butyl ether produced by the process of any one or more of the preceding aspects.

Aspect 20: A system for producing ethylene and at least one of butanol and an alkyl tert-butyl ether from field butane, comprising: an n-butanizer unit for separating the field butane into an n-butane stream and an isobutane stream; a cracker for cracking the n-butane stream to obtain a cracked product stream comprising n-butane, 1-butene, 2-butene, butadienes, or a combination comprising at least one of the foregoing; and at least one of the following: (1) a separation unit for separating the cracked product stream to obtain a butane stream and a butene stream, and a hydration unit for reacting the butene stream with water to obtain butanol, and (2) a dehydrogenation unit for dehydrogenating the isobutane stream to an isobutene stream and an ether synthesis unit for reacting the isobutene stream with an aliphatic alcohol to produce an alkyl tert-butyl ether.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

As used herein, the term "hydrocarbon" refers broadly to a substituent comprising carbon and hydrogen, optionally with 1 to 3 heteroatoms, for example, oxygen, nitrogen, halogen, silicon, sulfur, or a combination thereof.

The terms "fuel oxygenates," "gasoline oxygenates" and simply "oxygenates" refer to a class of gasoline additives that contain one or more oxygen atoms and are designed to improve the octane rating of gasoline increasing the oxygen content of the gasoline. Most oxygenates are either alcohols or ethers, for example methanol (MeOH), ethanol (EtOH), isopropyl alcohol (IPA), n-propyl alcohol (NPrOH), isobutanol (IBA), n-butanol (BuOH), sec-butyl alcohol (SBA), tert-butyl alcohol (TBA) or gasoline grade tert-butyl alcohol (GTBA), tert-amyl alcohol (TAA) or tert-pentanol, methyl tert-butyl ether (MTBE), ethyl tert-butyl ether (ETBE), tert-amyl methyl ether (TAME), tert-amyl ethyl ether (TAEE), tert-hexyl methyl ether (THEME) and diisopropyl ether (DIPE). These oxygenates can be produced by chemical and biological reactions that are known in the art, for example, chemical reaction between isobutylene and methanol or ethanol to produce MTBE or ETBE respectively, microbial fermentation of sugars to produce bio-ethanol, and the like. Production processes can further include purification, distillation, or dehydration steps to increase purity and to remove water.

"Fuel" refers to one or more alcohols, one or more hydrocarbons, one or more fatty esters, or a mixture thereof. In some embodiments, liquid alcohols are used. The fuel disclosed herein can be used to power internal combustion engines such as reciprocating engines (e.g., gasoline engines and diesel engines), Wankel engines, jet engines, some rocket engines, missile engines, and gas turbine engines. In some embodiments, the fuel comprises a mixture of alcohols such as butanol and pentanol.

"Fuel additive" refers to a minor fuel component such as chemical components added to fuels to alter the properties of the fuel, e.g., to improve engine performance, combustion efficiency, fuel handling, fuel stability, or for contaminant control. Types of additives include, but are not limited to, antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides, and combinations thereof.

A composition that is "substantially free" of a compound refers to a composition containing less than 20%, less than 10%, less than 5%, less than 4%, less than 3%, less than 2%, less than 1%, less than 0.5%, less than 0.1%, or less than 0.01% of the compound, based on the total volume or weight of the composition.

All test standards and methods, such as ASTM, AOCS, and ISO, are the most recent standard as of Nov. 20, 2018, unless specified otherwise.

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxys; $C_{6-10}$ aryloxy such as phenoxy; $C_{1-6}$ alkylthio; $C_{1-6}$ or $C_{1-3}$ alkylsulfinyl; C1-6 or $C_{1-3}$ alkylsulfonyl; aminodi($C_{1-6}$ or $C_{1-3}$)alkyl; $C_{6-12}$ aryl having at least one aromatic rings (e.g., phenyl, biphenyl, naphthyl, or the like, each ring either substituted or unsubstituted aromatic); $C_{7-19}$ arylalkyl having 1 to 3 separate or fused rings and from 6 to 18 ring carbon atoms; or arylalkoxy having 1 to 3 separate or fused rings and from 6 to 18 ring carbon atoms, with benzyloxy being an exemplary arylalkoxy.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A process for producing ethylene, a fuel additive, and, optionally, an alkyl tert-butyl ether from field butane, comprising:
   separating the field butane into an n-butane stream and an isobutane stream;
   cracking the n-butane stream to obtain a first cracked stream comprising ethylene and a cracked product stream comprising n-butane, 1-butene, 2-butene, butadienes, or a combination comprising at least one of the foregoing;
   separating the cracked product stream to obtain a butane stream and a butene stream comprising 1-butene and 2-butene, and reacting the butene stream with water to obtain a fuel additive comprising at least 50 weight percent 2-butanol, up to 30 weight percent tert-butanol, up to 15 weight percent $C_8$-hydrocarbons, provided the fuel additive comprises up to 5 weight percent di-sec-butyl ether, no greater that 0.5 weight percent $C_4$-hydrocarbons, and no greater than 500 ppm water, and, optionally, dehydrogenating the isobutane stream in a dehydrogenation unit to form an isobutene stream and reacting the isobutene stream with an aliphatic alcohol to produce an alkyl tert-butyl ether.

2. The process of claim 1, wherein the step of separating the field butane comprises distilling the field butane.

3. The process of claim 1, wherein the field butane comprises n-butane in an amount of 50 mole % to 80 mole %, based on the total moles of the field butane, and isobutane in an amount of 10 mole % to 50 mole %, based on the total moles of the field butane.

4. The process of claim 1, wherein the field butane comprises n-butane in an amount of 60 mole % to 75 mole % based on the total moles of the field butane, and isobutane in an amount of 20 mole % to 40 mole %, based on the total moles of the field butane.

5. The process of claim 3, wherein the field butane further comprises greater than 0 mole % to 5 mole % propane, based on the total moles of the field butane.

6. The process of claim 3, wherein the field butane further comprises 2 mole % to 3 mole % propane, based on the total moles of the field butane.

7. The process of claim 3, wherein the field butane further comprises greater than 0 mole % to 2.5 mole % isopentane, based on the total moles of the field butane.

8. The process of claim 3, wherein the field butane further comprises greater than 0 mole % to 1.5 mole % n-pentane, based on the total moles of the field butane.

9. The process of claim 3, wherein the field butane further comprises 0.5 mole % to 1.0 mole % n-pentane, based on the total moles of the field butane.

10. The process of claim 1, wherein the n-butane stream comprises n-butane in an amount equal to or greater than 85 mole %, based on the total moles of the n-butane stream.

11. The process of claim 1, wherein the n-butane stream comprises n-butane in an amount equal to or greater than 95 mole %, based on the total moles of the n-butane stream.

12. The process of claim 1, wherein the n-butane stream comprises n-butane in an amount of 100 mole %, based on the total moles of the n-butane stream.

13. The process of claim 1, wherein the isobutane stream comprises isobutane in an amount equal to or greater than 85 mole %, based on the total moles of the isobutane stream.

14. The process of claim 1, wherein the isobutane stream comprises isobutane in an amount equal to or greater than 93 mole %, based on the total moles of the isobutane stream.

15. The process of claim 1, further comprising hydrogenating the cracked product stream with hydrogen in the presence of a hydrogenation catalyst before the step of separating the cracked product stream.

16. The process of claim 1, further comprising recycling the butane stream to the step of separating the field butane.

17. The process of claim 1, wherein the alkyl tert-butyl ether comprises methyl tert-butyl ether, ethyl tert-butyl ether, or a combination comprising at least one of the foregoing.

18. The method of claim 1 comprising dehydrogenating the isobutane stream in a dehydrogenation unit to form an isobutene stream and reacting the isobutene stream with an aliphatic alcohol to produce an alkyl tert-butyl ether.

* * * * *